Figure 1:
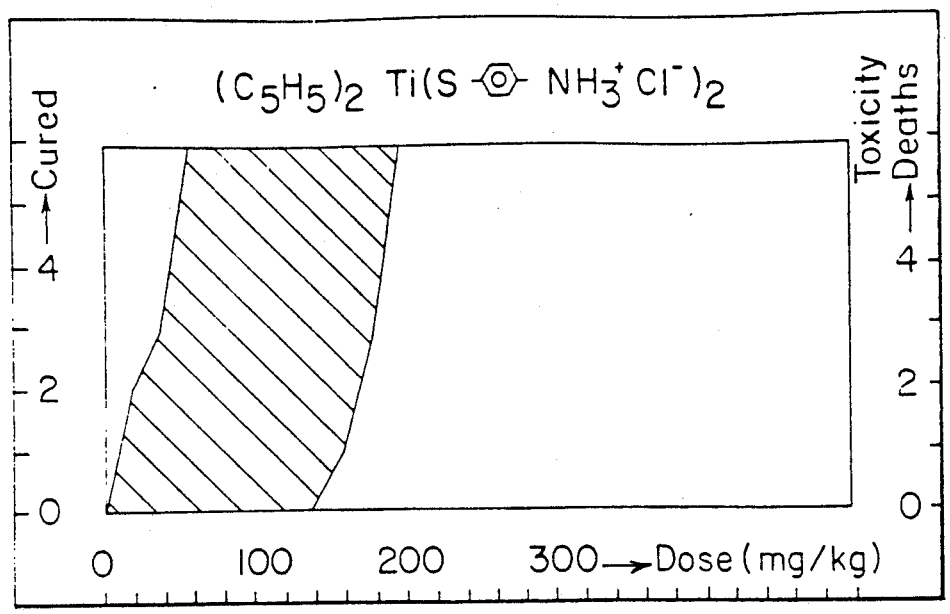
Figure 2:
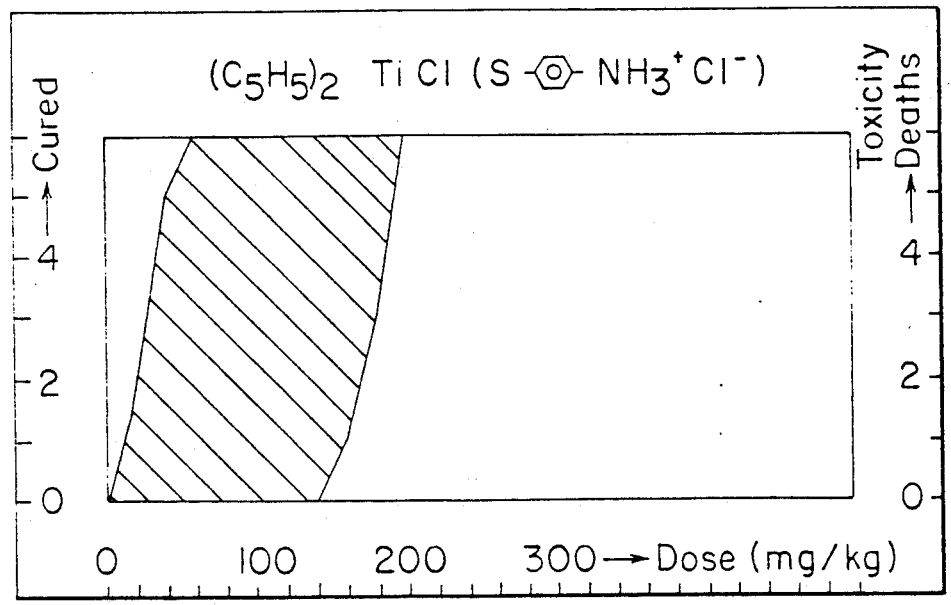
Figure 3:
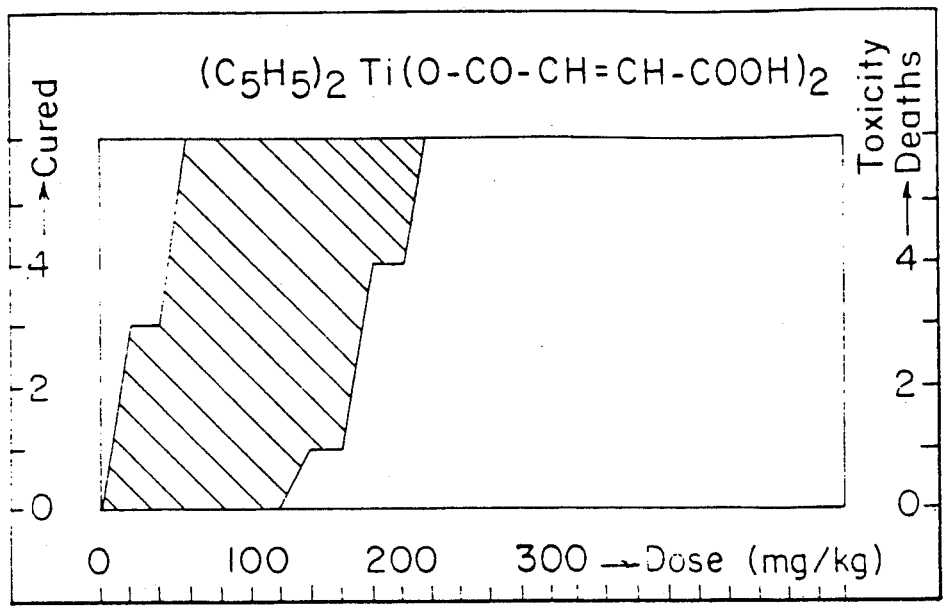
Figure 4:
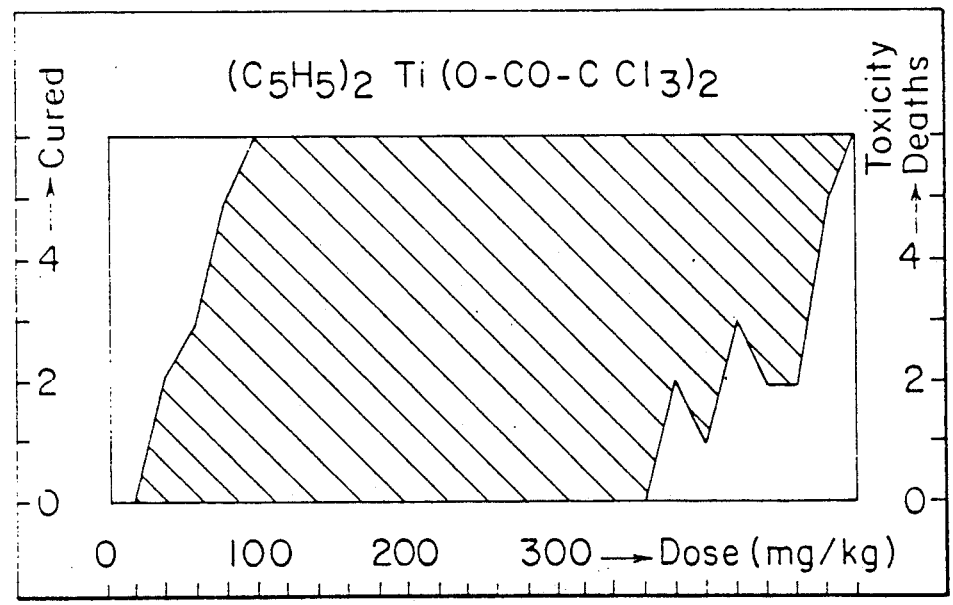
Figure 5:
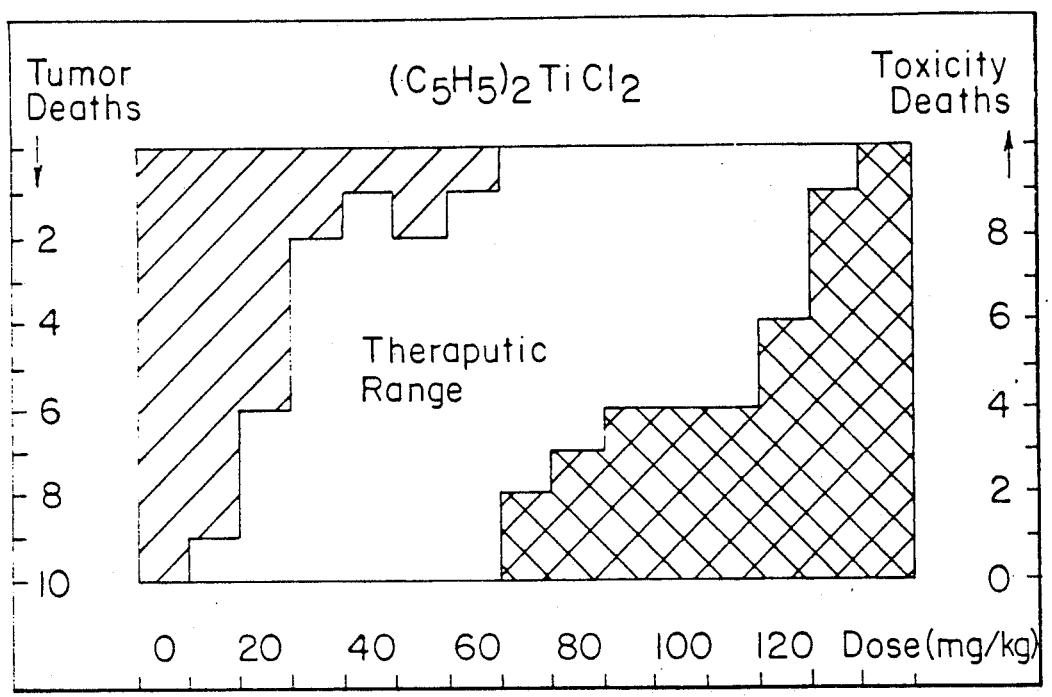

United States Patent [19]

Köpf-Maier et al.

[11] Patent Number: 5,002,969

[45] Date of Patent: Mar. 26, 1991

[54] PHARMACEUTICAL COMPOSITIONS CONTAINING TITANOCENE COMPLEXES AND USE OF THESE COMPLEXES AS CYTOSTATIC AGENTS

[76] Inventors: Petra Köpf-Maier; Hartmut Köpf, both of Bundesring 33, 1000 Berlin 42, Fed. Rep. of Germany

[21] Appl. No.: 866,077

[22] Filed: May 22, 1986

[30] Foreign Application Priority Data

May 22, 1985 [DE] Fed. Rep. of Germany ....... 3518447

[51] Int. Cl.[5] .............................................. A61K 31/28
[52] U.S. Cl. ................................................... 514/492
[58] Field of Search ......................................... 514/492

[56] References Cited

PUBLICATIONS

Döppert et al. (I), J. Organomet. Chem., 1982, 233, 205.
Doppert, (II), Makromol. Chem., Rapid Commun., 1980, 1, 519.

*Primary Examiner*—Jerome D. Goldberg
*Attorney, Agent, or Firm*—Birch, Stewart, Kolasch & Birch

[57] ABSTRACT

Titanocene complexes of the general formula I

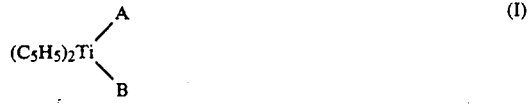

in which:
A is

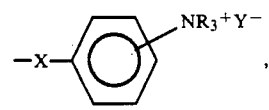

wherein
X is oxygen or sulfur,
R is hydrogen or $C_{1-4}$ alkyl and
Y is halogeno, or is —O—CO—R', wherein R' is —$CF_3$, —$CCl_3$, —$CBr_3$, —$CHCl_2$, —$CH_2Cl$, —CH=CH—COOH or —$(CH_2)_n$COOH and
n is an integer of 0, 1, 2, 3 or 4 and
B is halogeno or has the same meaning as A;
useful for the treatment of solid tumors.

9 Claims, 5 Drawing Sheets

PHARMACEUTICAL COMPOSITIONS CONTAINING TITANOCENE COMPLEXES AND USE OF THESE COMPLEXES AS CYTOSTATIC AGENTS

The present invention relates to titanocene complexes which show chemotherapeutic activity and, in particular, are useful for the treatment of solid tumors.

Cytostatically active metallocene complexes and pharmaceutical compositions containing these complexes have been described by the inventors in German patent 29 23 334. Further studies have revealed titanocene complexes which exhibit a higher therapeutic index (quotient of toxicity and activity) and which, therefore, are safer for therapeutic use.

These titanocene complexes have the following general formula

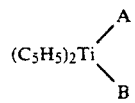  (I)

in which:
A is

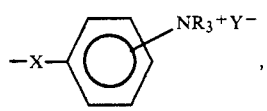

wherein
X is oxygen or sulfur,
R is hydrogen or C$_{1-4}$ alkyl and
Y is halogeno, or is —O—CO—R', wherein R' is —CF , —CCl , —CBr$_3$, —CHCl$_2$, —CH$_2$Cl, —CH=CH—COOH or —(CH$_2$)$_n$COOH and
n is an integer of 0, 1, 2, 3 or 4 and
B is halogeno or has the same meaning as A.

X is an oxygen or sulfur atom, preferably a sulfur atom. The substituent —NR$_3$+Y$^-$ may be in the ortho, meta or para position of the phenyl ring. R is a hydrogen atom or a C$_{1-4}$ alkyl group such as methyl, ethyl, n-propyl, isopropyl, n-butyl, tert.-butyl or isobutyl. Y is, for example, a fluorine, chlorine, bromine or iodine anion. B may be one of these halogen anions or have the meaning given above for A.

Representative examples of titanocene complexes of general formula I are:
(1) Bis(p-aminothiophenolato)bis($\eta^5$-cyclopentadienyl)-titanium(IV)-dihydrochloride
(2) p-Aminothiophenolato-chloro-bis($\eta^5$-cyclopentadienyl)-titanium(IV)-hydrochloride
(3) Bis(hydrogenmaleinato)bis($\eta^5$-cyclopentadienyl)-titanium(IV)
(4) Bis(trichloroacetato)bis($\eta^5$-cyclopentadienyl)titanium(IV)
(5) Bis(p-methylaminothiophenolato)bis($\eta^5$-cyclopentadienyl)-titanium(IV)-dihydroiodide
(6) Bis(p-ethylaminothiophenolato)bis($\eta^5$-cyclopentadienyl)-titanium(IV)-dihydroiodide
(7) Bis(m-diethylaminophenolato)bis($\eta^5$-cyclopentadienyl)-titanium(IV)-dihydrobromide
(8) o-Isopropylaminothiophenolato-iodo-bis($\eta^5$-cyclopentadienyl)titanium(IV)-hydroiodide
(9) Trifluoroacetato-fluoro-bis($\eta^5$-cyclopentadienyl)-titanium(IV)
(10) Hydrogensuccinato-bromo-bis($\eta^5$-cyclopentadienyl)titanium(IV)

These titanocene complexes are partly known and can be prepared according to methods described in the chemical literature.

Titanocene complexes of general formula I, in which A is

wherein X is oxygen or sulfur, R is hydrogen or C$_{1-4}$ alkyl and Y is halogeno, and wherein B is halogeno or has the same meaning as A, are new compounds.

These novel titanocene complexes may be produced by reacting a titanocene dihalogenide of general formula II

  (II)

in which Y has the meaning given above
(a) with an aminophenol or aminothiophenol compound of general formula III

  (III)

in which X and R have the meaning given above, to form a titanocene complex of general formula I or
(b) with a lithium-aminophenolate or aminothiophenolate of general formula IV

  (IV)

in which X and R have the meaning given above, to form a titanocene complex of general formula I'

  (I')

in which A' is

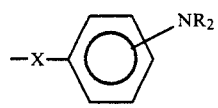

and B' is halogeno or has the same meaning as A', and reacting the titanocene complex of general formula I' thus obtained with a compound of general formula V

  (V)

in which X and R have the meaning given above, to form a titanocene complex of general formula I.

For the production of titanocene complexes of general formula I', wherein B is halogeno, a molar ratio of about 1:1 is employed in step (a) for II:III, and in step (b) for II:IV and I':V.

For the production of titanocene complexes of general formula I, wherein B has the same meaning as A, a molar ratio of about 1:2 is employed in step (a) for II:III, and in step (b) for II:IV and I':V.

The reactions may be carried out in suitable solvents such as, for example, water or organic solvents such as benzene, hexane or carbon tetrachloride and mixtures thereof. In step (b), the intermediate product of formula I' may be isolated or, alternatively, may be further reacted without isolation to form a titanocene complex of general formula I.

Below is a more detailed description of the production of titanocene complexes.

EXAMPLE 1

Production of
Bis(p-aminothiophenolato)bis($\eta^5$-cyclopentadienyl)-titanium(IV)-dihydrochloride (Compound 1)

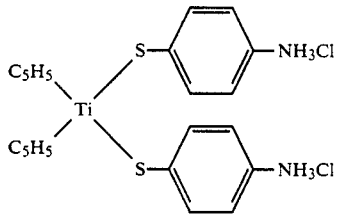

1.25 g (10 mmoles) of p-aminothiophenol in 40 ml of carbon tetrachloride are added dropwise within 30 minutes to a suspension of 1.25 g (5 mmoles) of titanocene dichloride in 10 ml of carbon tetrachloride. The mixture is stirred for 60 h at room temperature, whereafter the dark red compound is removed and washed with carbon tetrachloride. After drying in vacuo 2 3 g (yield 91%) of the fine crystalline compound 1 are obtained; Mp. > 135° C. (decomposition).

| $C_{22}H_{24}Cl_2N_2S_2Ti$ (MW 499,38) | | | | | |
|---|---|---|---|---|---|
| | C | H | Cl | N | S |
| calculated | 52,92 | 4,84 | 14,20 | 5,61 | 12,84% |
| found | 52,77 | 4,85 | 14,56 | 5,55 | 23,68% |

EXAMPLE 2

Production of
p-aminothiophenolato-chloro-bis($\eta^5$-cyclopentadienyl)-titanium(IV)-hydrochloride (Compound 2)

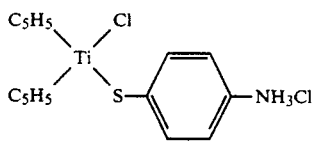

1.25 g (10 mmoles) of p-aminothiophenol in 50 ml of carbon tetrachloride are added dropwise within 1.5 h to a suspension of 2.5 g (10 mmoles) of titanocene dichloride in 80 ml of carbon tetrachloride. The mixture is stirred for 60 h at room temperature, whereafter the light violet-coloured compound is removed and washed with carbon tetrachloride. After drying in vacuo 3.4 g (yield 91%) of the fine crystalline compound 2 are obtained; Mp. > 115° C. (decomposition).

| $C_{16}H_{17}Cl_2NSTi$ (MW 374,19) | | | |
|---|---|---|---|
| | C | H | N |
| calculated | 51,36 | 4,58 | 3,74% |
| found | 50,97 | 4,52 | 3,68% |

EXAMPLE 3

Production of
Bis(hydrogenmaleinato)bis($\eta^5$-cyclopentadienyl)titanium(IV) (Compound 3)

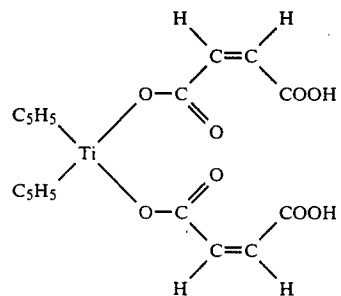

8 ml of an aqueous maleic acid solution saturated in the cold are added to a solution of 0.5 g (2 mmoles) of titanocene dichloride in 30 ml of hot water. Upon cooling, compound 3 crystallises in the form of macroscopic crystals of wine red colour. These are pressed between filter paper and 0.58 g (yield 71%) of compound 3, having analytical purity, are obtained; Mp > 200° C. (decomposition and decolorisation to brown).

| $C_{18}H_{16}O_8Ti$ (MW 408,22) | | |
|---|---|---|
| | C | H |
| calculated | 52,96 | 3,95% |
| found | 52,98 | 3,99% |

Reference: K. Döppert, R. Sanchez-Delgado, H.-P. Klein and U. Thewalt, J. Organomet. Chem., 1982, 233. 205

EXAMPLE 4

Production of
Bis(trichloroacetato)bis($\eta^5$-cyclopentadienyl)titanium(IV) (Compound 4)

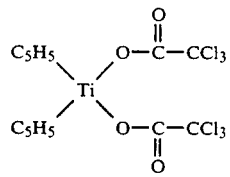

3.3 g (20 mmoles) of trichloroacetic acid are added to a solution of 0.5 g (2 mmoles) of titanocene dichloride in 30 ml of hot water, which results in an immediate precipitation of the orange-coloured compound 4. After the mixture has cooled, the compound is suction-filtered and washed with water. After drying in vacuo, 0.88 g (yield 88%) of compound 4 are obtained; Mp. 173°/174° C.

| $C_{14}H_{10}Cl_6O_4Ti$ (MW 502,78) | | |
|---|---|---|
| | C | H |
| calculated | 33,44 | 1,99% |
| found | 33,70 | 2,00% |

Reference: K. Döppert, Makromol. Chem., Rapid Commun., 1980, 1, 519

EXAMPLE 5

Production of Bis(p-methylaminothiophenolato)bis($\eta^5$-cyclopentadienyl)titanium(IV)-dihydroiodide (Compound 5)

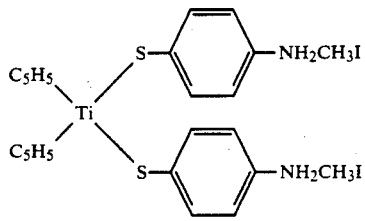

2.51 g (20 mmoles) of p-aminothiophenol are dissolved in 75 ml of benzene and converted into the lithium salt $LiSC_6H_4$-p-$NH_2$ by adding dropwise an equimolar amount (12.5 ml; 20 mmoles) of a hexane solution of n-butyllithium (c=1.6 mole/l) and stirring for 1 hour at 25° C. After addition of 2.50 g (10 mmoles) of $(C_5H_5)_2TiCl_2$, stirring is continued for 12 h and, subsequently, the stochiometric amount (1.25 ml; 20 mmoles) of $CH_3I$ (d=2,28 g/ml) is added dropwise. After stirring for additional 12 h at room temperature, the reaction solution is concentrated to dryness in vacuo and the residue is extracted for 8 h with 78 ml of hot $CH_2Cl_2$. The extraction solution is concentrated in vacuo to 20 ml and cooled at −20° C., whereafter the precipitated product is isolated by filtration and dried in vacuo for 24 h.

| | $C_{24}H_{28}I_2N_2S_2Ti$ | | |
|---|---|---|---|
| Analysis | C | H | N |
| calculated | 40,58 | 3,97 | 3,94% |
| found | 40,26 | 4,23 | 4,28% |

$^1$H-NMR (CDCl$_3$; δ in ppm): 7,20-6,50m(8), 6,35s(10), 3,55s,br(4), 2,42s(6).

IR (KBr/ν in cm$^{-1}$) 3300m,br, 3090w, 3030w, 2930w, 1612sh, 1590s, 1490vs, 1430s, 1275s,br, 1175m, 1095m, 1015s, 820vs, 705m, 635m,br.

EXAMPLE 6

Production of Bis(p-ethylaminothiophenolato)bis($\eta^5$-cyclopentadienyl)titanium(IV)-dihydroiodide (Compound 6)

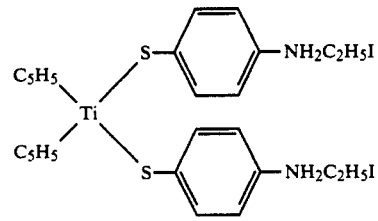

The compound is prepared in a manner analogous to that of compound 5 in example 5 using, however, 1.62 ml (20 mmoles) of $C_2H_5I$ (d=1.93 g/ml) instead of $CH_3I$.

Yield 3.98 g (54%) of fine crystalline product
Colour: black (solid), violet (in solution)

| | $C_{26}H_{32}I_2N_2S_2Ti$ | | |
|---|---|---|---|
| Analysis | C | H | N |
| calculated | 42,29 | 4,38 | 3,80% |
| found | 42,13 | 4,38 | 3,75% |

$^1$H-NMR (CDCl$_3$; δ in ppm): 6,77-6,40m(8), 6,24s(10), 3,52s,br(4), 2,69q(4), 1,14t(6).

IR (KBr/ν in cm$^{-1}$) 3380m,br, 2810w, 1678m, 1618s, 1590s, 1485s, 1435m, 1275s,br, 1175m, 1015m, 820vs, 690m,br.

The titanocene complexes according to the present invention are particularly useful for the treatment of solid tumors such as tumors of the digestive system as well as lung and breast carcinoma.

Activity against Ehrlich Ascites Tumor

Female CF$_1$ mice are each given about 6×10$^6$ Ehrlich ascites tumor cells by means of intraperitoneal injection and, 24 hours later, a single intraperitoneal dose of substance dose range of 20 to 500 mg/kg) in physiological saline solution (0.4 ml). In each case 5 to 10 animals are tested per dose. If appropriate, the preparation can be buffered to a pH of 4 to 7, for example with sodium bicarbonate or tris-(hydroxymethyl)-aminomethane, in order to avoid local irritation at the injection site. A group of untreated control animals which were injected intraperitoneally with 0.4 ml of physiological saline solution without administration of the substance is also run for each test series.

The tumor development in the individual dose ranges is evaluated by means of the weight course and survival time. The dose-dependent number of tumor deaths, toxicity deaths and surviving, and the associated percentage increase in the average survival time are determined for each substance.

The results obtained by testing compounds 1 to 4 as well as titanocene dichloride as a comparative substance are given in the following table I.

TABLE 1

| Compound Tested | Optimal Treating Rate | Therapeutic Index (LD$_{50}$/ED$_{90}$) |
|---|---|---|
| Compound 1 | 100% | 4,3 |

TABLE 1-continued

| Compound Tested | Optimal Treating Rate | Therapeutic Index ($LD_{50}/ED_{90}$) |
|---|---|---|
| Compound 2 | 100% | 4,4 |
| Compound 3 | 100% | 3,8 |
| Compound 4 | 100% | 5,5 |
| Titanocene-dichloride (Comparison) | 90-100% | 3,3 |

The test results are graphically illustrated in FIGS. 1 to 5.

As shown in these figures, the titanocene complexes according to the present invention exhibit a higher therapeutic index (corresponding to a greater therapeutic latitude) than titanocene dichloride. They are, thus, safer for therapeutic use. In addition, compounds 1, 2 and 3 have a better solubility in water than titanocene dichloride, which improves application and dosing.

Activity against ascitic and solid Sarcoma 180

The sarcoma 180 used in the present study was obtained from the Deutsche Krebsforschungszentrum (Heidelberg, Germany). It was propagated as an intraperitoneally growing tumor line on female NMRI mice which were kept under standard conditions (altromin food and tap water ad libitum, 12-h dark-light rhythm).

Antitumor testing was performed against sarcoma 180 in fluid ascitic as well as in solid, subcutaneously growing form. For testing against ascitic or solid sarcoma 180, the ascitic tumor of donor mice was harvested, diluted 1:3 (v:v) with saline and injected either into the peritoneal cavity or, subcutaneously, into the axillary region of female NMRI mice. Each animal obtained about $10^7$ tumor cells. The day of tumor transplantation was defined as day 0 of the experiment.

Before administration of the test compounds, samples corresponding to the applied doses were dissolved in DMSO, filled up with ninefold volumes of saline and applied to mice in volumes of 0.02 ml per g of body weight. The different doses were either given as a single injection on day 1 or as triple injections on days 1, 3 and 5. Details of dose levels and animal distribution are recorded in tables 2 and 3. The untreated, tumor-bearing control animals only received injections of the DMSO/saline mixture (0.02 ml/g). Every day occuring deaths were noted. Deaths within 8 days after tumor transplantation were defined as toxic deaths due to substance toxicity. In the case of ascitic sarcoma 180, the parameters evaluated were the values of mean survival time (MST) and of increase in life span (ILS); the latter was calculated by relating the mean survival time of a treated group to that of the corresponding control group expressed as a percentage and by subtracting 100%. The key date for the evaluation of the experiment and for determining the number of surviving (cured) animals was day 80. In the case of solid sarcoma 180, the tumors were removed on day 9 after transplantation and weighted to an accuracy of ±1 mg. From tumor weights of treated and control animals, the T/C ratios were calculated as follows:

$$T/C(\%) = \frac{\text{mean tumor weight of a dose group} \times 100}{\text{mean tumor weight of the control group}}$$

The following results were obtained:

TABLE 2

Activity against solid Sarcoma 180

| Compound | Dose (mg/kg) | Toxicity Deaths/Animals Treated | Tumor Weight[a] (g) | T/C (%) |
|---|---|---|---|---|
| Titanocene dichloride | 1 × 40 | —/5 | 1,31 ± 0,24 | 111 |
| | 1 × 50 | —/5 | 0,78 ± 0,34 | 66 |
| | 3 × 40 | —/5 | 0,75 ± 0,32 | 58 |
| | 3 × 50 | —/5 | 0,29 ± 0,14 | 23 |
| Titanocene dibromide | 1 × 50 | —/5 | 1,27 ± 0,37 | 108 |
| | 1 × 60 | —/5 | 1,21 ± 0,37 | 94 |
| | 3 × 50 | —/5 | 0,69 ± 0,17 | 53 |
| | 3 × 60 | 1/5 | 0,48 ± 0,10 | 37 |
| Compound 3 | 1 × 80 | —/5 | 1,13 ± 0,18 | 95 |
| | 1 × 120 | —/5 | 0,87 ± 0,41 | 73 |
| | 3 × 60 | —/5 | 0,91 ± 0,25 | 76 |
| | 3 × 100 | —/5 | 0,63 ± 0,14 | 53 |
| Compound 4 | 1 × 220 | —/5 | 1,14 ± 0,26 | 96 |
| | 1 × 320 | —/5 | 0,79 ± 0,28 | 67 |
| | 3 × 200 | —/5 | 1,26 ± 0,30 | 106 |
| | 3 × 300 | 1/5 | 0,44 ± 0,14 | 37 |
| Compound 1 | 1 × 60 | —/5 | 1,30 ± 0,30 | 109 |
| | 1 × 100 | —/5 | 1,03 ± 0,26 | 86 |
| | 3 × 60 | —/5 | 0,47 ± 0,12 | 39 |

[a]Given are mean values and standard deviations

TABLE 3

Activity against ascitic Sarcoma 180

| Compound | Dose (mg/kg) | Toxicity Deaths/Animals Treated | MST[b] (d) | ILS (%) | Survivors/Animals Treated |
|---|---|---|---|---|---|
| Titanocene dichloride | 1 × 40 | —/6 | 27,3 (20–49) | 32 | —/6 |
| | 1 × 40 | —/5 | 32,0 (18–80) | 81 | 1/5 |
| | 1 × 50 | —/6 | 54,0 (25–80) | 161 | 3/6 |
| | 1 × 50 | —/5 | 50,0 (25–80) | 184 | 2/5 |
| Titanocene dibromide | 1 × 50 | —/5 | 28,4 (22–34) | 61 | —/5 |
| | 1 × 60 | —/5 | 40,2 (20–80) | 128 | 1/5 |
| Compound 3 | 1 × 80 | —/5 | 32,2 (15–80) | 95 | 1/5 |
| | 1 × 120 | —/5 | 37,2 (21–80) | 125 | 1/5 |
| Compound 4 | 1 × 220 | —/5 | 17,2 (15–20) | 4 | —/5 |
| | 1 × 320 | —/5 | 32,4 (18–80) | 96 | 1/5 |
| Compound 1 | 1 × 60 | —/5 | 19,0 (15.25) | 15 | —/5 |
| | 1 × 100 | —/5 | 39,4 (19–80) | 139 | 1/5 |

[b]Given are mean values of survival time, in parenthesis the range of single values

Activity against B16 Melanoma and Colon 38 Carcinoma

The B16 melanoma and colon 38 carcinoma used were obtained from the NCI Liasion Office, Institut Jules Bordet, Brussels, Belgium and, for propagation, were kept as solid, subcutaneously growing tumor lines on male C57BL/6J mice. For testing, the tumors were transplanted to female $B_6D_2F_1$ mice. All animals were kept under standard conditions (22°–23° C., tap water and altromin food ad libitum, 12-h light-dark rhythm).

For tumor transplantation on day 0 of the testing experiments, solid tumors were removed from donor mice, minced with scissors and reduced to small particles. After suspension in twofold volumes of Hank's balanced salt solution, volumes of 0.3 ml were inoculated subcutaneously into the axillary region, resulting in the growth of solitary solid tumors.

The test compounds were administered either as a single injection on day 1 or as three injections on days 1, 3 and 5, or as five injections on days 1, 3, 5, 7 and 9. The different doses applied and the animal distribution are recorded in table 4. The substances, dissolved or suspended in a DMSO-saline mixture (1/9=v/v), were always injected intraperitoneally. The concentrations were selected in such a manner that each mouse received a total volume of 0.4 to 0.5 ml. Control animals only obtained one, three or five injections of the DMSO-saline mixture (0.5 ml/animal) without drug addition.

The number of deaths was recorded daily. Deaths occuring within 7 days (single injection), 11 days (three injections) or 15 days (five injections) after tumor transplantation were defined as deaths due to substance toxicity.

In the case of B16 melonoma, the tumors were removed and weighed on day 10 for the single and three injections or on day 15 for the five injections. Colon 38 carcinomas were always evaluated on day 15 of the experiment.

The antitumor activity, expressed as T/C values, is shown in the following table 4.

TABLE 4

Activity against B16 Melanoma and Colon 38 Adenocarcinoma

| Compound | Dose (mg/kg) | T/C (%) B16 Melanoma | Colon 38 Carcinoma |
|---|---|---|---|
| Titanocene dichloride | 1 × 50 | 61 | 41 |
|  | 3 × 40 | 69 | 28 |
|  | 3 × 50 | 37 | — |
| Titanocene dibromide | 1 × 60 | 42 | 36 |
|  | 3 × 50 | 48 | 51 |
|  | 3 × 60 | 44 | — |
| Compound 1 | 1 × 100 | 80 | 61 |
|  | 3 × 60 | 36 | 38 |
| Compound 3 | 1 × 120 | 89 | 72 |
|  | 3 × 100 | 50 | 50 |
| Compound 4 | 1 × 320 | 85 | 48 |
|  | 3 × 300 | 41 | — |

Activity against Heterotransplanted Human Tumors

The same testing procedure as in the tests with B16 melanoma and colon 38 carcinoma was employed. The test compounds were applied in equivalent and equitoxic doses, subdivided into five injections. The first injection was administered on day 8 (mammary carcinoma), day 10 (adenocarcinoma of rectum and lung) and day 26 (small cell lung carcinoma) of the tumor transplantation. The T/C values were determined 3 days after the last substance injection, i.e., on day 23 (mammary carcinoma), day 25 (adenocarcinoma of rectum and lung) and day 41 (small cell lung carcinoma).

The results obtained are shown in table 5.

TABLE 5

Activity against some Heterotransplanted Human Tumors

| Compound | Dose (mg/kg) | T/C (%) (based on mean relative volume of tumor) | | | |
|---|---|---|---|---|---|
|  |  | Rectum Adeno- carci- noma | Lung Adeno- carci- noma | Lung Small Cell Carcinoma | Mammary Carci- noma |
| Titanocene dichloride | 5 × 15 | 38 | 34 | 110 | 49 |
| Titanocene dibromide | 5 × 20 | 48 | 53 | 96 | 44 |
| Compound 1 | 5 × 50 | 59 | 49 | 83 | 49 |
| Compound 3 | 5 × 30 | 89 | 35 | 65 | 40 |

Figure 6:
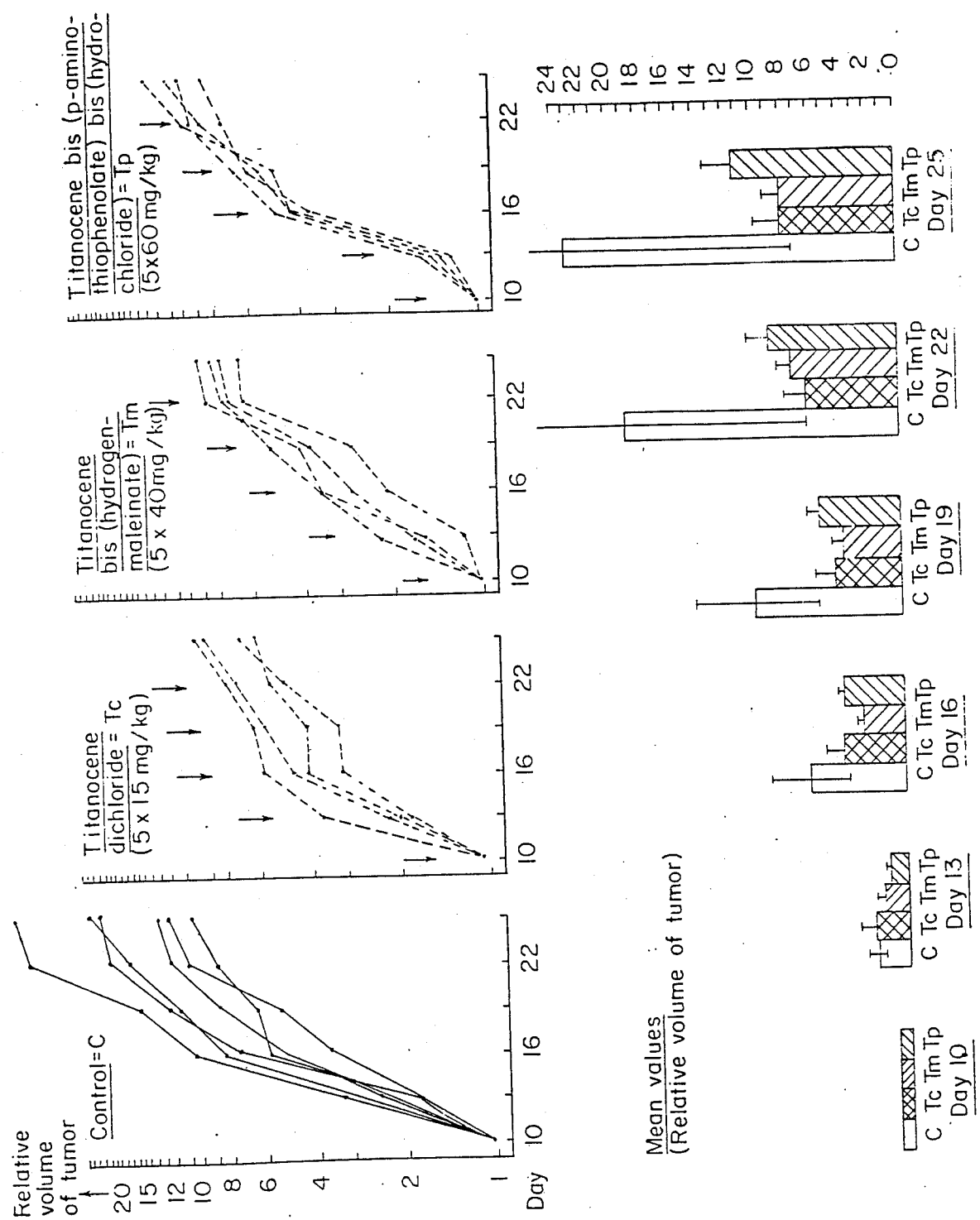
Figure 7:
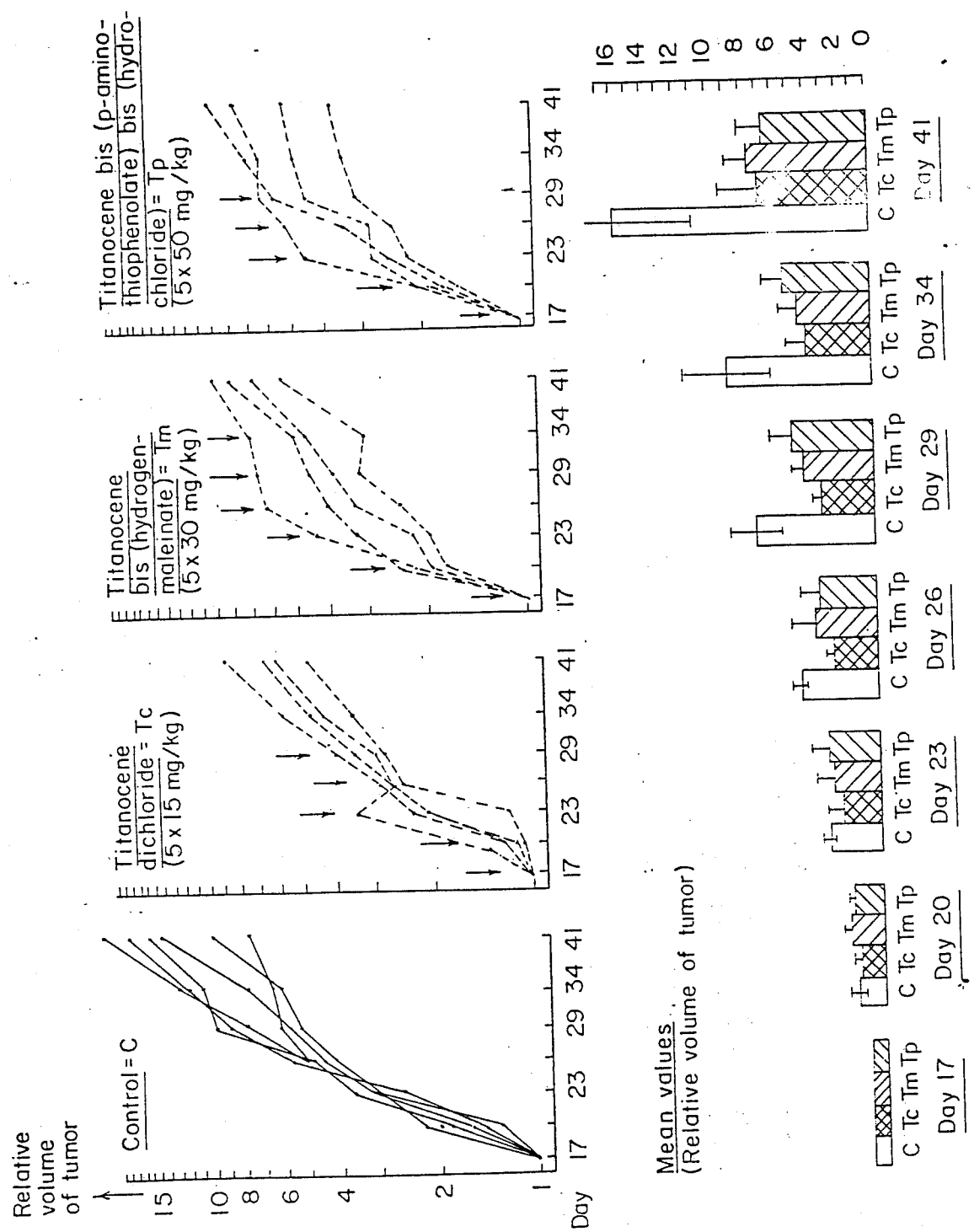

The results obtained in the testing with adenocarcinoma of the lung and the rectum are graphically illustrated in FIGS. 6 and 7.

For combating solid tumors, the titanocene complexes according to the present invention may be employed as such or as pharmaceutical compositions containing at least one titanocene complex of the general formula I, in addition to pharmaceutically acceptable excipients, diluents and/or auxiliary agents. The pharmaceutical formulations of the active compounds are preferably in the form of unit doses matched to the particular mode of administration. A unit dose can be, for example, a tablet, a capsule, a suppository or a measured volume of powder, granules or a solution or suspension. "Unit dose" is understood as meaning a physically specific unit containing an individual amount of the active compound mixed with a suitable pharmaceutical excipient, diluent and/or auxiliary. The amount of active compound is chosen here so that one or more units are usually sufficient for an individual therapeutic administration.

The unit does can also be divisible, for example in the form of grooved tablets, if only a fraction, for example one half or one quarter, of the divisible unit is required for an individual therapeutic administration. The medicaments of the invention contain, if they are in the form of a unit dose, 1 to 10 000 mg, preferably 5 to 7 500 mg, of active compound.

The medicaments of the invention are preferably used orally, rectally or parenterally, for example intravenously, subcutaneously, intramuscularly, intrapleurally, intraperitoneally, intrafocally or perifocally. The therapeutic administration can be effected continuously by means of infusion over several hours or by one to several individual administrations or individual injections. The administration sequence and the dose administered can vary greatly as a function of the nature and stage of the disease and depending on the treatment regime, in particular on the number and dosage level of combination products administered. For example, initial treatment can be performed with 200 to 800 mg i.v. daily or with individual doses, for example 10 to 40 mg/kg i.v., at corresponding intervals, and subsequent long-term treatment can be carried out with 1 to 4 tablets, each of 50 mg of active compound.

The medicaments as a rule consist of the active compounds according to the invention and non-toxic, pharmaceutically acceptable medicament excipients, which are used as an admixture in solid, semi-solid or liquid form or as a coating agent, for example in the form of a capsule, a tablet coating, a sachet or another container for the active compound. The excipient can serve here, for example, as an agent for promoting absorption of the medicament by the body or as a formulation auxiliary, sweetener, flavoring agent, colorant or preservative.

Tablets, coated tablets, hard and soft gelatin capsules, dispersible powders, granules, aqueous and oily suspensions, emulsions, solutions and syrups, for example, are suitable for oral administration.

Tablets can contain inert diluents, such as calcium carbonate, calcium phosphate, sodium phosphate or lactose; granulating and distributing agents, such as starch, gelatin or gum acacia; and lubricants, such as aluminum stearate, magnesium stearate, talc or silicone oil. If appropriate, the tablets can be provided with a coating, which can also be such that it effects delayed dissolution and absorption of the medicament in the gastrointestinal tract and thus, for example, a better tolerance or longer period of action.

Gelatin capsules can contain the active compound mixed with a solid diluent (for example calcium carbonate or kaolin) or an oily diluent (for example olive oil, arachis oil or paraffin oil).

Examples of suitable suspending agents are sodium carboxymethylcellulose, methylcellulose, hydroxypropylcellulose, sodium alginate, polyvinylpyrrolidone, gum tragacanth or gum acacia; examples of suitable dispersing agents and wetting agents are polyoxyethylene stearate, heptadecaethyleneoxycetanol, polyoxyethylenesorbitol monooleate, polyoxyethylenesorbitan monooleate and lecithin; examples of suitable preservatives are methyl and propyl hydroxybenzoate; and examples of flavoring agents and sweeteners are sucrose, lactose, dextrose and invert sugar syrup. Oily suspensions can contain, for example, arachis, olive, sesame, coconut or paraffin oil and thickeners, such as beeswax, hard paraffin or cetyl alcohol, sweeteners, flavoring agents and/or antioxidants.

Water-dispersible powders and granules contain the active compound mixed with dispersing agents, wetting agents and suspending agents, for example the abovementioned substances and/or dimethyl sulfoxide, and with sweeteners, flavoring agents and/or colorants.

Emulsion can contain, for example, olive, arachis or paraffin oil, in addition to emulsifiers, such as gum acacia, gum tragacanth, phosphatides, sorbitan monooleate or polyoxyethylenesorbitan monooleate, sweeteners and/or flavoring agents.

Suppositories which are prepared with the aid of binders which melt at rectal temperature, for example cocoa butter or polyethylene glycols, are suitable for rectal use.

The medicaments can be administered parenterally as sterile isotonic saline solutions or other solutions. A solubilizing agent, such as dimethyl sulfoxide, may be added in order to achieve a uniform solution or suspension, but this is usually not necessary.

In all the presentation forms, the medicaments of the invention can also contain buffer substances, for example sodium bicarbonate or tris(hydroxymethyl)aminomethane.

Besides the titanocene complexes according to the invention, the medicaments can contain one or more other pharmacologically active constituents from other groups of medicaments, for example alkylating agents, antimetabolites and cytostatic alkaloids, antibiotics, enzymes and heavy metal compounds. The medicaments can, furthermore, optionally contain immunosuppressant substances and vitamins. The additional substances mentioned can also be added to the active compounds according to the invention in separate pharmaceutical formulations as combination products.

The active compound content of the medicaments is usually 0.01 to 95% by weight, preferably 0.1 to 85% by weight, based on the finished medicament.

What is claimed is:

1. A cytostatic pharmaceutical composition comprising 0.01 to 95% by weight of a titanocene complex of the formula I $$(C_5H_5)_2Ti\diagdown^A_B \qquad (I)$$

in which:
A is $$-X-\phi-NR_3^+Y^-$$

wherein
X is oxygen or sulfur,
R is hydrogen or $C_{1-4}$ alkyl and
Y is halogeno, or is $-O-CO-R'$, wherein R' is $-CF_3$, $-CCl_3$, $-CBr$, $-CHCl_2$, $-CH_2Cl$, $-CH=CH-COOH$ or $-(CH_2)_nCOOH$ and n is an integer of 0, 1, 2, 3 or 4 and
B is halogeno or has the same meaning as A, or mixtures thereof; and a sterile, nontoxic pharmaceutically acceptable carrier.

2. A method for the treatment of solid tumors in an animal which comprises administering to said animal an effective tumor growth inhibiting amount of the composition according to claim 1, said animal having a tumor susceptible to said titanocene complex.

3. A method for treating cancer in an animal which comprises administering to said animal a cytostatic effective amount of the composition according to claim 1, said animal having a cancer susceptible to said titanocene complex.

4. A pharmaceutical composition according to claim 1, wherein said titanocene complex is selected from the group consisting of:
Bis(p-aminothiophenolato)bis($\eta^5$-cyclopentadienyl)-titanium(IV)-dihydrochloride
p-Aminothiophenolato-chloro-bis($\eta^5$-cyclopentadienyl)-titanium(IV)-hydrochloride
Bis(p-methylaminothiophenolato)bis($\eta^5$-cyclopentadienyl)-titanium(IV)-dihydroiodide
Bis(p-ethylaminothiophenolato)bis($\eta^5$-cyclopentadienyl)-titanium(IV)-dihydroiodide
Bis(m-diethylaminophenolato)bis($\eta^5$-cyclopentadienyl)-titanium(IV)dihydrobromide and
o-Isopropylaminothiophenolato-iodo-bis($\eta^5$-cyclopentadienyl)titanium(IV)-hydroiodide, or mixtures thereof.

5. A method for the treatment of solid tumors in an animal which comprises administering to said animal an effective tumor growth inhibiting amount of the composition according to claim 4, said animal having a tumor susceptible to said titanocene complex.

6. A method for treating cancer in an animal which comprises administering to said animal a cytostatic effective amount of the composition to claim 4, said animal having a cancer susceptible to said titanocene complex.

7. A pharmaceutical composition according to claim 1, wherein said titanocene complex is selected from the group consisting of:
Bis(hydrogenmaleinato)bis($\eta^5$-cyclopentadienyl)-titanium(IV)
Bis(trichloroacetato)bis($\eta^5$-cyclopentadienyl)titanium(IV) and
Trifluoroacetato-fluoro-bis($\eta^5$-cyclopentadienyl)-titanium(IV), or mixtures thereof.

8. A method for the treatment of solid tumors in an animal which comprises administering to said animal an effective tumor growth inhibiting amount of the composition according to claim 7, said animal having a tumor susceptible to said titanocene complex.

9. A method for treating cancer in an animal which comprises administering to said animal a cytostatic effective amount of the composition according to claim 4, said animal having a cancer susceptible to said titanocene complex.

* * * * *